US006303113B1

(12) United States Patent
Woog et al.

(10) Patent No.: US 6,303,113 B1
(45) Date of Patent: *Oct. 16, 2001

(54) PROCESS FOR THE PRODUCTION OF PHARMACEUTICAL PREPARATIONS CONTAINING HUMAN PROTEIN FOR INFUSION OR INJECTION PURPOSES

(75) Inventors: Heinrich Woog, Laudenbach; Werner Gruber, Birkenau; Hans-Jörg Markl, Ellerstadt; Gerhard Winter, Dossenheim; Fritz Demmer, Hirschberg, all of (DE)

(73) Assignee: Roche Diagnostics GmbH, Mannheim (DE)

( * ) Notice: Subject to any disclaimer, the term of this patent is extended or adjusted under 35 U.S.C. 154(b) by 0 days.

This patent is subject to a terminal disclaimer.

(21) Appl. No.: 08/593,579

(22) Filed: Jan. 30, 1996

Related U.S. Application Data

(63) Continuation-in-part of application No. 08/193,002, filed as application No. PCT/EP92/01822 on Aug. 10, 1992, now Pat. No. 5,503,827.

(30) Foreign Application Priority Data

Aug. 15, 1991 (DE) .................................................. 41 26 983

(51) Int. Cl.⁷ ............................ A61K 38/19; A61K 38/22
(52) U.S. Cl. ................................ 424/85.1; 514/8; 514/12
(58) Field of Search .................................... 514/12, 21, 8; 424/85.1; 530/350, 351, 380, 395, 397, 399, 829

(56) References Cited

U.S. PATENT DOCUMENTS

| 4,992,419 | 2/1991 | Woog et al. ............................. 514/8 |
| 5,503,827 | * 4/1996 | Woog et al. ........................ 424/85.1 |
| 5,661,125 | 8/1997 | Strickland ................................ 514/8 |

FOREIGN PATENT DOCUMENTS

| 0 058 903 | 9/1982 | (EP) . |
| 0 306 824 | 9/1988 | (EP) . |
| 2 177 914 | 2/1987 | (GB) . |
| WO 91/01143 | 2/1991 | (WO) . |

OTHER PUBLICATIONS

Roth et al., *Hagers Manual of the Pharmaceutical Practices*, vol. 7, "Pharmaceutical Formulations and Ingredients Section A: Pharmaceutical Formulations" and partial English translation.

* cited by examiner

Primary Examiner—Robert A. Schwartzman
(74) Attorney, Agent, or Firm—Arent Fox Kintner Plotkin & Kahn, PLLC

(57) ABSTRACT

The present invention concerns a process for the production of well-tolerated, preserved injection or infusion solutions containing human protein.

15 Claims, No Drawings

PROCESS FOR THE PRODUCTION OF PHARMACEUTICAL PREPARATIONS CONTAINING HUMAN PROTEIN FOR INFUSION OR INJECTION PURPOSES

This application is a continuation-in-part of U.S. Ser. No. 08/193,002, filed Feb. 15, 1994, now U.S. Pat. No. 5,503,827.

The present invention is concerned with a process for the production of pharmaceutical preparations containing human protein or use as an infusion or injection solution in a well-tolerated form.

In the meaning of the present invention, human proteins are endogenous proteins occurring in only small amounts which are used for therapeutic purposes such as e.g. t-PA (tissue plasminogen activator), G-CSF (granulocyte colony stimulating factor), streptokinase, urokinase, interferon or EPO (erythropoietin) and their recombinantly-produced derivatives including deletion, insertion and substitution variants which on the whole have similar or comparable pharmacological properties.

Pharmaceutical preparations containing human protein are described, in the European Patent Application EP 0 430 200 for subcutaneous or intramuscular administration which, by means of the addition of amino acids, have a better bioavailability and are better tolerated in comparison with known forms of administration.

Stabilized pharmaceutical preparations containing human protein which contain inter alia, urea and various amino acids, are known from EP 0 306 824, in which EPO and G-CSF in particular are mentioned by way of example as human proteins.

Furthermore in EP 0 456 153 galenic aqueous formulations of EPO are described for the production of injection preparations for subcutaneous or intramuscular administration which have a pH value of 6–8 and solely contain an alkali metal phosphate or alkali metal halide for stabilization.

The production of the above-mentioned human proteins by genetic engineering is known for example from the following Patent Applications: processes are described in the PCT applications WO 85/02610 and WO 86/03520 for the production of rh-EPO (recombinant human erythropoietin) by genetic engineering. Furthermore, the production of polypeptides with erythropoietin-like action is described in EP 0 409 113; EP 0 357 804; WO 86/02100 and WO 91/05867. Furthermore, processes are known from the prior art for the production of other recombinant proteins, for example of polypeptides with plasminogen activator-like action from WO 90/09437; EP 0 227 462; EP 0 400 545 or EP 0 440 763. The production of polypeptides with G-CSF-like action is known for example from EP 91 107 429.2; PCT/EP 91/00192; EP 169,566; WO 86/04506 (Chugai Seiyaku); EP 215,126 (Chugai Seiyaku); and WO 87/01132 (Kirin-Amgen) which are herein incorporated by reference into the present application. As used in the present invention, the term G-CSF-like activity means that the protein has the same biological activity as G-CSF.

EPO is a glycoprotein which stimulates the formation of haemoglobin and erythrocytes in the bone marrow. This lipoprotein is mainly formed in the kidney, is present in a very small amount in the serum and is excreted under physiological conditions in the urine. As used in the present application, the term erythropoietin-like activity means that the protein has the same biological activity as erythropoietin. Such proteins have at least the primary structural conformation of human EPO which allows possession of the biological property of causing bone marrow cells to increase production of recticulocytes and red blood cells and to increase hemoglobin synthesis or iron uptake. Proteins with erythropoietin-like activity are described in EP 205,564, EP 0 411 678 and EP 148 605 which are herein incorporated by reference into the present application.

However, it has been ascertained that injection or infusion solutions containing human protein from different manufacturers were tolerated differently due to different compositions in the galenic formulation or due to small structural differences in the active substances with regard to the amino acid sequence or to the glycosylation pattern of the protein. Although the solutions known from the prior art were essentially isotonic solutions which themselves should be well-tolerated without major problems, unpleasant side effects were observed when they were administered. When for example injection solutions containing EPO were administered, patients often complained about pains at the point of injection which occurred during and after the administration. Depending on the particular galenic formulation used, burning pains frequently occurred in many patients especially when those injection solutions were used which contained human serum albumin and citrate buffer as additives for stabilization. In some cases, the patients developed a high temperature, high blood pressure, urticaria, back pain, nausea and also shock.

Furthermore it has been shown that injection solutions with a relatively low content of active substance cannot be adequately stabilized. Thus for example pharmaceutical formulations which contained EPO as the human protein in an amount of for example 500 to 20,000 U, are not sufficiently stable. It could be shown that some galenic formulations favored the undesired formation of aggregates or agglomerates of the human proteins especially when stored for longer periods. Consequently, immunological problems can arise when such preparations are used.

The previous pharmaceutical preparations known from the prior art which contain human proteins are formulations which as a rule do not contain preservatives since they are generally used for a single administration in the form of a so-called single-dose formulation or single dose container. In contrast, so-called multi-dose units or multi-dose containers are suitable for a multiple administration in any desired partial amounts of the active substance. Special demands are thereby made on the stability and storability of such forms of administration, especially with regard to the sterility of the solutions. For this reason such solutions are provided with preservatives in order to prevent the growth of micro-organisms in the prepared injection or infusion solution ready for administration.

However, the production of preserved pharmaceutical preparations containing human protein has proven to be difficult. When preservatives are used it has been shown that these give rise to stability problems if the pharmaceutical preparations are stored for longer periods. In this process the human proteins are inactivated and agglomerates are formed which may be the cause of the observed intolerance to the injection solutions. The usual processes for the production of preserved pharmaceutical formulations for infusion or injection purposes cannot be used in the case of active human protein ingredients since the active substances are inactivated under the sterilization conditions in autoclaves at 121° C. for 20 minutes and their structure is destroyed. It is also known that the usual preservatives used in pharmacy react with the active human protein ingredients and these are thereby inactivated. For this reason intravenous (i.v.) or subcutaneous (s.c.) preparations were previously produced as single-dose formulations under aseptic conditions without a preservative having been used in this case.

Thus, the problem existed of finding a process for the production of preserved pharmaceutical preparations containing human protein for injection or infusion purposes by means of which pharmaceutical preparations can be produced which do not have the above-mentioned disadvantages. It should be possible to administer these pharmaceutical preparations produced in this manner in a reproducible, well-tolerated manner. They should ensure an administration which is as pain-free as possible and should be germ-free. Furthermore multi-dose forms of administration (multi-dose containers) should be provided which are germ-free and can be administered with good tolerance.

This object is achieved in that in a process for the production of pharmaceutical preparations containing human protein for injection or infusion purposes, preservatives are added at a concentration of up to 2% (weight % to volume %, w/v; the conversion factor from w/v % to mg/ml is 10, i.e., 0.1%=1 mg/ml.) and especially 0.01 to 1% or 0.1 to 0.3% and, if desired, these are removed again before production of the storable pharmaceutical formulation. By selecting those preservatives which have a very low allergy rate, it is additionally possible to also leave such preservatives in the storable pharmaceutical preparation so that a selective removal is not absolutely necessary.

The pharmaceutical preparations produced in this manner are preserved, i.e. they contain preservatives or a preservative was present during their production for at least part of the time. All substances which act bactericidally can be used for the preservation. The preservatives employed inhibit the growth of microorganisms which get into the preparation during the filling or even kills them.

In the process according to the present invention, it is especially advantageous when those preservatives are used which can readily be removed in one of the last process steps for the production of the storable pharmaceutical formulation. This has the advantage that the administrable pharmaceutical preparations are then free from any preservatives influencing the tolerance. The volatile preservatives that are especially advantageous for this include chloretone (chlorobutanol, 1,1,1-trichloro-2-methyl-2-propanol), benzyl alcohol, p-chloro-m-cresol and pyrocarbonic acid dialkyl esters of the general formula R—O—CO—O—CO—O—R in which R represents a $C_1$–$C_6$ alkyl group, in particular a methyl, ethyl, propyl or tert.-butyl.

However, even when the preservative is co-administered, the effects on the tolerance can be minimized. After it had been ascertained that different preservatives with the same preserving action have a different allergy rate, the tolerance can be improved by the correct choice of the agent. Preservatives with a low allergy rate are in particular, chlorobutanol, benzyl alcohol and benzalkonium chloride. Benzalkonium chloride stands for a mixture of quaternary ammonium compounds (quats) of the alkylbenzyl-dimethylammonium chloride type of the general formula [$H_5C_6$—$CH_2$—$N^+(CH_3)_2R$]Cl in which R is an alkyl residue $C_8H_{17}$–$C_{18}H_{37}$ for example benzododecinium chloride or cetalkonium chloride (cf. Kirk-Othmer 2: 633 ff; 19: 562 ff.).

Furthermore these preservatives have the advantage that they do not inactivate the human proteins present in the solution. The tolerance is also improved by a concentration of the preservative which is as low as possible. In particular the content of an individual preservative in the pharmaceutical solution should be between 0.001–20 mg/ml and preferably does not exceed a 0.001 value of 10 mg/ml. Up to 5 mg/ml of a preservative are preferably used in the pharmaceutical solution.

The required concentration can be minimized by various measures. For example by preventing the inactivation of the human protein by the preservative to as great an extent as possible. This has the further advantage that the stability of the injection solution is increased. The inactivation can be inhibited by selecting the preservative with regard to a low reactivity. The inactivation is additionally reduced when the contact between the human protein and the preservative is as short as possible. The necessary concentration of the preservative in the solution can also be reduced by preventing its absorption to materials, for example to rubber, with which the solution comes into contact.

The type of preservative used plays an important role for the tolerance. All preservatives have a greater or lesser allergy rate. It is, however, not always possible to avoid their use in order to guarantee freedom from microorganisms. According to the investigations forming the basis of the patent application, it is possible to use the preservatives in the production of the injection solutions in such a way that not only is a greatest possible freedom from microorganisms guaranteed but also side-effects of the preservatives are almost completely excluded.

In spite of the fact that the added preservatives react to a greater or lesser extent with the human proteins and thereby inactivate them it is not possible in many cases to completely omit the addition of preservatives since microorganisms can enter the solution for example during the filling process or because, when an injection solution is prepared from a sterile lyophilisate in a multi-dose container, this must be preserved until it has been completely used up.

The addition of preservative is not a problem in the production of a preparation when the preservative is selected so that it vaporizes or sublimes away during the lyophilization. Preservatives which have an appropriate volatility are for example chloretone and benzyl alcohol.

According to one embodiment of the process of the present invention, the human proteins are dissolved in water with the necessary auxiliary substances, the necessary amounts of preservatives (up to a maximum of 2%) are added and if necessary, heated to the temperature which the human protein in question can withstand as regards stability, without it being thereby inactivated. The preservative is allowed to take effect for a longer period of time until the solution is substantially germ-free, i.e. up to about 4 hours and preferably 10 minutes to 2 hours. Afterwards the solution of active substance is dispensed into bottles and lyophilized. As a rule the preservative sublimes away or evaporates during the lyophilization. The lyophilisates obtained in this way produce a sterile solution for infusion or injection purposes after reconstitution with conventional solvents.

The good tolerance of the human protein injection solution is influenced inter alia by the correct choice of the pH value, of the buffer capacity, of the titration acidity and of the buffer substances present in the solution.

The upper pH value of the solution should not lie substantially above the neutral point (the pH value of blood is from 7.2 to 7.4) because human proteins are not stable in the alkaline range. For intravenous administration the solutions preferably have a pH value of about 4.5–7.4. Solutions with a pH value of about 6–7.4 are preferred for subcutaneous administration. The intravenous and subcutaneous administration differ because, due to the intravenous inflow of blood and the buffers present in the blood, a quicker adjustment to physiological pH conditions is possible than can take place subcutaneously. Since the rate of adjustment in the case of subcutaneous and intravenous administration can also be improved by a lowest possible buffer capacity and a titration acidity which is as low as possible the acceptable minimum value of the pH value of the solution also depends upon these parameters. In this case the buffer capacity of the solution ready for administration is in the range 0–10 mVal/l and the titration acidity in the range 0–20 mVal/l. In particular, the buffer capacity of the solution ready for administration should not be more than 6 mVal/l and the titration acidity not more than 10 mVal/l.

The buffer capacity is generally defined as that equivalent amount (Val) of acid or lye which is necessary in order to change the pH value of a solution with a volume of one liter by one pH unit. If monobasic acids or bases are used for the titration the specification Val/l for the acid or base used corresponds to the molar amount mol/l of this acid. Since in the present case the solutions used have a pH value in the acid range the buffer capacity can alternatively be defined as that amount of for example a 0.1 N NaOH solution which is needed in order to increase the pH value of a solution of one liter by one pH unit. The pharmaceutical solutions containing human protein contain the usual pharmaceutical auxiliary substances and vehicles during the determination of the buffer capacity.

The determination of the buffer capacity of the pharmaceutical preparations containing human protein is carried out on the injection or infusion solutions ready for administration which, in addition to the active substance itself, contain conventional auxiliary substances and additives for pharmaceutical practice. As a rule the solutions have an acidic pH value for the stabilization of the protein. The corresponding amount of base which is necessary to increase the pH value of the solution by one pH unit is determined by titration with bases.

Preferred limits for the buffer capacity in the infusion or injection solution for intravenous administration are up to 2.4 ml of a 0.1 N sodium hydroxide solution and preferably up to 0.5 ml. This corresponds to an amount of lye of 0.24 mmol or 0.05 mmol. For subcutaneous administration it is preferable to use up to 1 ml of a 0.1 N NaOH solution and especially up to 0.2 ml of a 0.1 N NaOH solution. This corresponds to an amount of lye of up to 0.1 mmol or up to 0.02 mmol.

Furthermore, it has been shown that it is advantageous when the injection or infusion solutions ready for administration have a titration acidity which is as low as possible, of up to 5 mVal/l.

Preferred limits for the titration acidity of the infusion or injection solutions for intravenous administration are up to 10 ml, preferably up to 5 ml, 3 ml or 1 ml of a 0.1 N NaOH solution. This corresponds to a titration acidity of up to 1 mmol/l or up to 0.3 mmol/l or 0.1 mmol/l. For subcutaneous administration it is preferable to use up to 5 ml, especially up to 2 ml or up to 0.5 ml of a 0.1 N NaOH solution. In this case the titration acidity is 0.5 mmol/l or up to 0.2 mmol/l or 0.05 mmol/l.

The titration acidity or basicity is generally defined as that amount of lye or acid which is necessary in order to adjust the pH value of a solution with a volume of one liter to the pH value of blood (about 7.2 to 7.4). In the present case the titration acidity can alternatively be defined as that amount of for example a 0.1 N NaOH solution which is necessary to increase the pH value of one liter of a solution to that of blood (about 7.3). The pharmaceutical solutions containing human protein contain the conventional pharmaceutical auxiliary substances and additives during the determination of the buffer capacity. The method for the determination of the titration acidity is carried out in a manner analogous to that for the determination of the buffer capacity by starting with the injection or infusion solution ready for administration and determining that amount of base which is necessary in order to adjust the pH value of the solution to about 7.

The usable pH range for an infusion or injection solution and that can be administered substantially pain-free is in the acid or neutral range depending on the particular human protein used. The infusion or injection solutions have a pH value in the range of about 2–7.4. Solutions are preferably used with a pH value of about 3.8–7.4, whereby the pH values 4.5 to 6.0 and preferably 5.5 to 6.0 come into particular consideration as the lower limit. pH values of the solutions are preferably used as the upper limit of the pH range which are close to the pH value of blood. Solutions are preferably used for intravenous applications with a pH value of 6–7.4, in particular 6.8–7.2. Solutions are preferably used for subcutaneous applications with a pH value of 6.5–7.2, in particular 7.0–7.2.

Suitable muteins can also be used in addition to the naturally-occurring form of the human proteins. The term "muteins" is generally understood as those human proteins whose amino acid sequence differs by at least one amino acid from the natural sequence. These differences can be for example that one or more and preferably 1 to 10 amino acids in the natural 10 sequence are replaced by other amino acids or that one or more amino acids are added to or even omitted from the N- or C-terminal end. This is then referred to as N- or C-terminal extensions or N- or C-terminal deletions. The above-mentioned possibilities may, if desired, also be combined with one another, i.e. the N-terminal end of the natural sequence can for example be elongated while simultaneously shortening the C-terminal end during which, if desired, it is also possible to simultaneously replace one or more amino acids by other amino acids. With regard to the particular direction of indication the fragments thus obtained should have substantially the same fundamental therapeutic properties and actions as the natural human proteins.

In general the term "recombinant" refers to those human proteins which are produced with the aid of recombinant DNA technology. These methods encompass the cloning of the gene that codes for the particular human protein, the insertion of appropriate cDNA or genomic DNA into a suitable vector such as e.g. into bacterial plasmids and the transformation of these recombinant plasmids into suitable host cells. The cloned gene is then expressed in the host cell and the corresponding human protein is isolated in a known manner.

The liquid or also the lyophilized pharmaceutical preparations may, if desired, contain conventional pharmaceutical auxiliary substances such as stabilizing agents or organic hydrophilic polymers. Oligosaccharides such as sucrose, tetralose, lactose, dextrans with a molecular weight of about 10,000 to 2,000,000 are for example suitable as stabilizers. Organic hydrophilic polymers are macromolecules with a carbon backbone which is made up of hydrophilic monomeric units, if desired, with polar side groups such as polyethylene glycol or polyvinylpyrrolidone.

The pharmaceutical preparations additionally contain conventional pharmaceutical buffers such as alkali phosphates (sodium or potassium phosphate or their hydrogen or dihydrogen salts), salts of organic or inorganic acids or amino acids. The composition of the various buffer substances in the formulation is chosen so that a buffer capacity which is as low as possible results, of the injection or infusion solution ready for administration. This can be achieved by using an amount of buffer substances which is as low as possible and in doing so the total amount of the buffer should in particular not exceed a concentration of 100 mmol/l in the pharmaceutical solution. Buffer substances are preferably used at a concentration of 10 to 100 mmol/l and especially of 20 to 60 mmol/l. Alternatively, it is also possible to select the individual buffer substances such that they mutually compensate their action that is mainly in the acid or basic buffer range. In this case the total amount of buffer substances can be up to 200 mmol/l in the final administrable pharmaceutical preparation.

The lyophilized pharmaceutical preparations preferably additionally contain a structure former which forms a crystalline matrix when the aqueous solution freezes, that also remains structurally stable during the subsequent lyophilization and during storage of the lyophilisate for longer periods under various external conditions. In this sense mannitol and glycine come into consideration as suitable structure formers.

The pharmaceutical preparations produced in this manner are preferably marketed in the form of lyophilisates. They can be used as single dose preparations, in which case a particular amount of the human protein is present in an injection bottle, ampoule or capsule and the lyophilisate is dissolved by the addition of an appropriate amount of reconstitution solution. The reconstitution solution can already contain the required amount of lye that is needed to adjust the desired pH value of the injectable solution. In addition conventional isotonic additives can also be used. The lyophilisate can, on the other hand, also contain wholly or partly the amounts of basic reagents required to set the advantageous pH range so that the reconstitution is carried out essentially with distilled water for injection purposes. Furthermore, the lyophilisate as well as also the reconstitution solution can contain agents which ensure the production of an isotonic solution. The reconstituted solution is then drawn up into an injection syringe and can be administered directly into the patient. So-called single dose preparations contain for example rh-EPO in an amount of 500 to 20,000 U and preferably 1000, 2000, 5000, 10,000 or 15,000 U. When a proportionately larger amount of human protein is used it is also possible to produce multi-dose preparations. In this case, a larger volume (about 5 to 10 ml) is used as the reconstitution solution and this solution can then be used for several administrations. In this case the amount of human protein to be administered can be decided individually by the physician or it can be used for several administrations in different patients.

The specific activity of the EPO used for the production of the injection or infusion solutions is preferably about 160,000 IU per absorbance unit at 280 nm (cf. EP 0 209 539).

Injection solutions containing human protein contain, in addition to the active substance, conventional auxiliary substances which include, besides the aforementioned stabilizers, buffers, complexing agents and wetting agents dissolved in water. The buffers are used at concentrations of about 1 to about 100 mmol/l. Usable pH values of the solutions are between about 4.5 and about 7.4 in the case of intravenous administration and between about 6.0 and about 7.4 in the case of subcutaneous administration. The upper limit lies in the pH value range of blood (7.2 to 7.4). Higher pH values are to be avoided because the human proteins are usually not stable in the alkaline range.

In the following, the present invention is described in detail on the basis of examples. rh-EPO and G-CSF as representatives of the class of human proteins are used in each case as the active substance. However, other human proteins can also be used in the same way.

In order to produce injection solutions that can be used in the present invention, the auxiliary substances are dissolved in water in a sterile V2A double-jacketed tank equipped with a stirrer. The essential auxiliary substances are buffers, complexing agents, stabilizers and wetting agents. Suitable buffers for setting the physiologically optimum range for intravenous and subcutaneous use are in particular glycocoll sodium citrate, primary potassium phosphate, secondary sodium phosphate, carbonate and salts of amino acids, as well as the sodium and potassium salts of malic acid, maleic acid, fumaric acid, tartaric acid and aspartic acid and combinations of these substances. The buffers are used at a concentration of about 1 to about 100 mmol/l solution. The active substance is added to the solution and it is made up to the final volume and stirred. The batch solution is sterilized by filtration over a membrane filter with a pore size of 0.2 $\mu$m. The solution obtained in this way is dispensed in 0.5 ml aliquots into injection bottles under aseptic conditions and subsequently dried in a lyophilization unit.

The formulations described above are also stable as solutions ready for injection. In their production the solution obtained is not lyophilized but rather dispensed directly into an ampoule or injection bottle with a volume of for example 1 ml per container.

Conventional pharmaceutical auxiliary substances or additives are used to produce the pharmaceutical forms of administration that contain the human proteins. Stabilizing or solubilizing agents such as the basic amino acids arginine, lysine or ornithine can also be added. Glycine, leucine, isoleucine, threonine, glutamine, glutamic acid, aminoacetic acid, phenylalanine as well as further amino acids mentioned in the Patent Applications EP 0 430 200 and EP 0 306 824 are used in particular as amino acids which serve to stabilize or solubilize the protein and can in addition be used as buffer substances. The form of administration can be marketed as a lyophilisate or also as a ready-to-use infusion or injection solution.

When preserving the injection solutions according to the present invention a distinction has to be made between whether a formulation is for single-dose containers or one for multi-dose containers.

Since the preservatives conventionally used in pharmacy react with the human proteins and inactivate them, preparations for intravenous and subcutaneous administration are often produced as single-dose formulations under aseptic conditions without in this process using a preservative. However, it is not always possible to avoid the entry of some micro-organisms into the preparation during the filling process which can give rise to damage if their growth is not inhibited or they are killed by the addition of a preservative. In order to prevent the preservative from inactivating the human protein or causing an allergy when administered, a preservative is used according to the invention in the case of single-dose formulations that is eliminated before storage of the formulation during the lyophilization of the solution i.e. is evaporated or sublimed. Such preservatives are for example chloretone, benzyl alcohol, p-chloro-m-cresol and diethyl pyrocarbonate, the first of them and the latter being preferably used. The usable concentrations are between 0.1 and about 2.0 and preferably between 0.1 and about 0.3%. The exact concentration depends on the concentration of active substance and is determined from case to case by methods well-known to a person skilled in the art.

It is a legal requirement that formulations in multi-dose containers for intravenous and subcutaneous administration must be adequately preserved i.e. that even on the last day of the stipulated storage period a preserving action must still be present to a full extent. In order to satisfy this requirement the human protein solution in injectable form must contain preservatives. This gives rise to problems because as stated above, the preservatives react with the human proteins and induce a sensitization in patients. The reaction with the active substance leads, on the one hand, to a reduction of the activity of the active substance and, on the other hand, of the preserving action which is further reduced by absorption of preservatives to rubber stoppers.

According to the present invention these difficulties are countered by using preservatives which do not react very much with human proteins and have little sensitizing action, by aiming for the shortest possible contact between the human protein and the preservative and excluding factors which contribute to a consumption of preservative.

Examples of less reactive and sensitizing preservatives are chlorobutanol, benzyl alcohol, benzalkonium chloride and combinations of these substances. When the said preservatives are used individually the following concentrations are employed: chlorobutanol: 2.0 to 5.0 mg/ml, preferably 3.0 to 4.0 mg/ml; benzyl alcohol: 1.0 to 5.0 mg/ml, preferably 2.0 to 3.0 mg/ml; benzalkonium chloride: 0.01 to 0.05 mg/ml, preferably 0.02 to 0.03 mg/ml.

It has turned out that it is particularly advantageous to use combinations of the individual preservatives. A better preservation is achieved by this means and the disadvantageous interactions with human proteins are minimized. Preferred combinations are solutions which contain in particular benzyl alcohol/benzalkonium chloride, benzyl alcohol/chlorobutanol or chlorobutanol/benzyl alcohol/ benzalkonium chloride. In this case chlorobutanol is preferably used up to a concentration of 10 mg/ml, benzyl alcohol up to 10 mg/ml and benzalkonium chloride up to 0.1 mg/ml, in particular 0.001 to 0.05 mg/ml. The combined use of benzyl alcohol and benzalkonium chloride is particularly advantageous in which case the concentration of benzyl alcohol is preferably 3 to 6 mg/ml and that of benzalkonium chloride 0.01 to 0.025 mg/ml in the pharmaceutical solution.

The concentration of the human protein in the pharmaceutical preparation is preferably equal to or lower than the sum of the concentrations of all of the preservatives in the preparation. The ratio of the human protein to the preservative should be between 1:1–1:1000, preferably between 1:1–1:100 and more preferably between 1:5–1:50. When the protein is EPO the ratio should be 1:1–1:50. When the protein is G-CSF the ratio should be 1:10–1:30. The concentration of the human protein should be between 0.001–5 mg/ml, preferably between 0.01–1 mg/ml, and more preferably between 0.01–0.5 mg/ml. When the human protein is erythropoietin (EPO), the concentration is preferably 0.005–1 mg/ml, more preferably 0.01–0.5 mg/ml and most preferably 0.025–0.1 mg/ml. The concentration of EPO in units/ml is preferably 5000–100,000 units/ml and preferably 5,000–20,000 units/ml which corresponds to 0.025–0.5 mg/ml, preferably 0.025–0.1 mg/ml. The specific activity of EPO is in the range of 100,000–200,000 Int. units (IU)/absorption unit (AU) at 280 nm (cf. EP 209,539), preferably 160,000 IU/AU. The specific activity in terms of U/mg can be calculated by multiplication of the above value for IU/AU with the factor 1.35 (i.e. 160,000 IU/AU corresponds to 216,000 U/mg). The EPO used in the examples had an activity of 200,000 U/mg. A particularly preferred preparation contains 0.1 mg/ml EPO; 0.02 mg/ml benzalkonium chloride and 4 mg/ml benzyl alcohol.

When the human protein is G-CSF, the concentration is preferably 0.01–2 mg/ml and more preferably 0.1–0.5 mg/ml.

The use of less reactive and less sensitizing preservatives and the short period of contact already help to reduce the necessary amount of preservative because this minimizes the degradation of the preservative when the human protein is inactivated.

The shortest possible contact is ensured in that the formulation in a lyophilisate form or in a concentrated form—if desired after the preservative has been removed during lyophilization (see above)—is stored under sterile conditions and the preservative is not added until the injection form is prepared whereby the injection solution should be consumed within 30 days.

If a lyophilisate is chosen, the pharmaceutical package unit can additionally contain the solvent needed for reconstitution. As a rule these are matched to the corresponding lyophilisate in such a way that injectable solutions are obtained on mixing which have the properties according to the present invention. The lyophilisate can already contain wholly or partly the necessary amounts of preservatives so that the reconstitution is essentially carried out with distilled water for injection purposes. On the other hand it is in principle also possible that the reconstitution solution contains the necessary amount of preservative in order to obtain preserved injectable pharmaceutical solutions.

This is the preferred variant in the case of the multidose preparations.

In the manufacture of the pharmaceutical package units it is usual to provide the forms of administration with a package insert which inter alia contains instructions that the infusion or injection solutions enable well tolerated and pain-free administration.

It is intended to use the following examples to describe in more detail human protein solutions according to the invention for multi-dose containers and their production. The solutions in question are those which contain EPO or G-CSF as human protein. However, other human proteins can also be used in the same way. The formulations produced are present as lyophilisates or as liquid preparations which remain stable for years when stored in a refrigerator at about +4 to about +8° C.

EXAMPLE 1

EPO 2000 Units Injection Dry Substance (Batch for 35,000 Bottles)

The following auxiliary substances are dissolved in a sterile 100 l V2A double-jacketed tank equipped with a stirrer:

| | | | |
|---|---|---|---|
| urea | 700.0 g | 70.0 g | 0 g |
| sodium chloride | 70.0 g | 70.0 g | 70.0 g |
| Tween 20 | 7.0 g | 7.0 g | 7.0 g |
| chloretone | 70.0 g | 70.0 g | 70.0 g |
| sodium dihydrogen phosphate × 1H2O | 38.4 g | 38.4 g | 38.4 g |
| disodium hydrogen phosphate × 2H$_2$O | 350.0 g | 350.0 g | 350.0 g |
| calcium chloride × 2H$_2$O | 8.4 g | 0.42 g | — |
| glycine | 105.0 g | 105.0 g | 105.0 g |
| L-leucine | 140.0 g | 140.0 g | 140.0 g |
| L-isoleucine | 140.0 g | 140.0 g | 140.0 g |
| L-threonine | 35.0 g | 35.0 g | 35.0 g |
| L-glutamic acid | 35.0 g | 35.0 g | 35.0 g |

-continued

| | | | |
|---|---|---|---|
| L-phenylalanine | 70.0 g | 70.0 g | 70.0 g |
| water for injection purposes ad | 70.0 l | 70.0 l | 70.0 l |

214.3 ml of an erythropoietin raw material batch with an EPO titre of 140,000 units/1 ml is added to 30 l of this solution of auxiliary substances and then made up to a final volume of 35 l and stirred. The filtration system is rinsed with the remainder of the solution of auxiliary substances. The batch solution is sterilized by filtration over a membrane filter of 0.2 μm pore size. The sterile-filtered solution is dispensed in 1 ml aliquots into injection bottles under aseptic conditions and freeze-dried in a lyophilization unit.

The formulations described in the example are stable when stored not only as lyophilisates but also as injectable solutions.

EXAMPLE 2

EPO Lyophilisate 1000 Units (Batch for 35,000 Bottles)

| Components: | | | |
|---|---|---|---|
| erythropoietin | 233.33 ml = 35 million units | | |
| sodium chloride | 100.0 g | 100.0 g | 100.0 g |
| Tween 20 | 12.0 g | 12.0 g | 12.0 g |
| diethyl pyrocarbonate | 210.0 g | 210.0 g | 210.0 g |
| sodium dihydrogen phosphate × 1H$_2$O | 140.0 g | 140.0 g | 140.0 g |
| disodium hydrogen phosphate × 2H$_2$O | 50.0 g | 50.0 g | 50.0 g |
| calcium chloride × 2H$_2$O | 10.0 g | 0.5 g | — g |
| urea | 700.0 g | 0.0 g | 0.0 g |
| glycine | 1050.0 g | 1050.0 g | 1050.0 g |
| L-leucine | 92.0 g | 92.0 g | 92.0 g |
| glutamic acid | 103.0 g | 103.0 g | 103.0 g |
| phenylalanine | 115.5 g | 115.5 g | 115.5 g |
| water for injection purposes ad | 70.0 l | 70.0 l | 70.0 l |

The auxiliary substances are dissolved in 70 l of water for injection purposes and subsequently divided into two portions of 35 l. The necessary amount of EPO active substance is added to the first 35 l. The second 35 l are used to rinse the filtration system. The batch solution is sterilized by filtration over a membrane filter of 0.2 μm pore size. The sterile-filtered solution is dispensed in 1 ml aliquots into injection bottles under aseptic conditions and lyophilized under the same criteria as given in example 1, during which the diethyl pyrocarbonate evaporates. In this way a white porous lyophilisate is obtained which is readily soluble in 2 ml of water and can be stored for 3 years in a refrigerator or for 1 year at room temperature without great loss of activity.

G-CSF and rPA solutions can for example also be produced in the same manner during which, however, the dissolution of the solution components and the sterile filtration are carried out while gassing with nitrogen.

EXAMPLE 3

EPO Lyophilisate 5000 U and 10,000 U

| Components: | | |
|---|---|---|
| erythropoietin | 5000 U | 10,000 U |
| calcium chloride × 2H$_2$O | 0.151 mg | 0.302 mg |
| sodium chloride | 2.500 mg | 5.000 mg |
| polysorbate 20 | 0.250 mg | 2.500 mg |
| sodium dihydrogen phosphate × 1H$_2$O | 1.190 mg | 2.380 mg |
| disodium hydrogen phosphate × 2H$_2$O | 9.965 mg | 19.930 mg |
| aminoacetic acid | 37.500 mg | 75.000 mg |
| L-leucine | 5.000 mg | 10.000 mg |
| L-isoleucine | 5.000 mg | 10.000 mg |
| L-threonine | 1.250 mg | 2.500 mg |
| L-glutamic acid | 1.250 mg | 2.500 mg |
| L-phenylalanine | 2.500 mg | 2.500 mg |
| water for injection purposes ad | 2.14 — 5.35 ml | 4.18 — 10.70 ml |

The production of the lyophilisates is carried out analogously to the procedure described in Example 1 with the sole difference that before the lyophilization the solution is dispensed into 0.5 ml bottles and not into 1 ml bottles.

These lyophilisates are dissolved before use with well tolerated reconstitution solutions containing preservatives: 5.0 mg chlorobutanol, ad 1.0 ml water for injection purposes. Alternatively it is also possible to use solutions of benzyl alcohol (about 4–5 mg/ml) with the addition of benzalkonium chloride (about 0.01 to 0.05 mg/ml).

EXAMPLE 4

EPO Solutions Ready-for Injection

| Components: | 1000 U/ ampoule | 2000 U/ ampoule | 5000 U/ ampoule | 10,000 U/ ampoule |
|---|---|---|---|---|
| EPO | 1000 U | 2000 U | 5000 U | 10,000 U |
| urea | 5.00 mg | 5.00 mg | 5.00 mg | 5.00 mg |
| polysorbate 20 | 0.10 mg | 0.10 mg | 0.10 mg | 0.10 mg |
| NaCl | 0.50 mg | 0.60 mg | 0.60 mg | 0.60 mg |
| NaH$_2$PO$_4$, 2H$_2$O | 0.31 mg | 0.62 mg | 0.62 mg | 0.62 mg |
| Na$_2$HPO$_4$, 12H$_2$O | 5.03 mg | 10.06 mg | 10.06 mg | 10.06 mg |
| CaCl$_2$, 2H$_2$O | 0.04 mg | 0.08 mg | 0.08 mg | 0.08 mg |
| aminoacetic acid | 7.50 mg | 15.00 mg | 15.00 mg | 15.00 mg |
| L-glutamic acid | 0.25 mg | 0.50 mg | 0.50 mg | 0.50 mg |
| L-isoleucine | 1.00 mg | 2.00 mg | 2.00 mg | 2.00 mg |
| L-leucine | 1.00 mg | 2.00 mg | 2.00 mg | 2.00 mg |
| L-phenylalanine | 0.50 mg | 1.00 mg | 1.00 mg | 1.00 mg |
| L-threonine | 0.25 mg | 0.50 mg | 0.50 mg | 0.50 mg |
| water for injection purposes ad | 1 ml | 1 ml | 1 ml | 1 ml |

The production process differs from that used in Example 3 only in that the solution obtained is not lyophilized but rather dispensed directly into an ampoule or injection bottle in an amount of 0.5 ml per container.

These injection solutions are diluted before use with 0.5 ml or 1.0 ml of a preserved, well-tolerated solution of the following composition: 5.0 mg benzyl alcohol; water for injection purposes ad 1.0 ml. Alternatively it is also possible to use solutions of benzyl alcohol (about 4–5 mg/ml) with addition of benzalkonium chloride (about 0.01–0.05 mg/ml).

EXAMPLE 5

Formation of Oligomers

Pharmaceutical preparations containing rh-EPO were investigated with regard to their tendency to form oligomers. For this the formulations known from the prior art were compared with the formulations according to the present invention. The pharmaceutical preparations were stored as lyophilisates at various temperatures for a longer period of time and subsequently reconstituted with distilled water. The proportion of oligomers in the formulations in percent was determined by Western blotting. In the case of formulations which contained human serum albumin and citrate, aggregates were found in amounts of 16%, 8% and 3% depending on the manufacturer whereas the solutions produced by the process according to the present invention were practically free from aggregates.

EXAMPLE 6 rhG-CSF Solutions with pH 2.5

| | |
|---|---|
| rhG-CSF | 0.175 mg |
| sodium chloride | 1.500 mg |
| polysorbate 80 | 0.050 mg |
| aminoacetic acid analytical quality | 5.750 mg |
| L-leucine | 0.500 mg |
| L-isoleucine | 0.500 mg |
| L-threonine | 0.125 mg |
| L-glutamic acid | 0.125 mg |
| L-phenylalanine | 0.250 mg |
| HCl 0.1 molar | 0.000 mg |
| water for injection purposes | +493.025 mg | pH value of the solution reconstituted in 0.5 ml of water for injection purposes: 2.5.

These injection solutions are diluted before use with 0.5 ml or 1.0 ml of a preserved, well-tolerated solution of the following composition: 5.0 mg benzyl alcohol, water for injection purposes ad 1.0 ml. Alternatively it is also possible to use solutions of benzyl alcohol (about 4–5 mg/ml) with addition of benzalkonium chloride (about 0.01–0.05 mg/ml).

EXAMPLE 7

G-CSF Formulations with pH Value 4.5

| | |
|---|---|
| rhG-CSF | 0.175 mg |
| sodium chloride | 1.500 mg |
| polysorbate 80 | 0.050 mg |
| aminoacetic acid analytical quality | 6.550 mg |
| L-leucine | 0.500 mg |
| L-isoleucine | 0.500 mg |
| L-threonine | 0.125 mg |
| L-glutamic acid | 0.125 mg |
| L-phenylalanine | 0.250 mg |
| NaOH 0.1 molar ad pH 4.5 | 0.000 mg |
| water for injection purposes | +492.225 mg | pH value of the solution reconstituted in 0.5 ml water for injection purposes: 4.5. These injection solutions are diluted before use with 0.5 ml or 1.0 ml of a preserved, well-tolerated solution of the following composition: 5.0 mg benzyl alcohol, water for injection purposes ad 1.0 ml. Alternatively it is also possible to use solutions of benzyl alcohol (about 4–5 mg/ml) with addition of benzalkonium chloride (about 0.01–0.05 mg/ml).

Buffer capacity: 3.0 mmol/l NaOH (30 ml 0.1 N NaOH)

Titration acidity: 5.0 mmol/l NaOH (50 ml 0.1 N NaOH).

EXAMPLE 8

G-CSF Formulation with pH Value 3.8–4.0

| | |
|---|---|
| rhG-CSF | 0.175 mg |
| sodium chloride | 1.500 mg |
| polysorbate 80 | 0.050 mg |
| aminoacetic acid, analytical quality | 5.750 mg |
| L-leucine | 0.500 mg |
| L-isoleucine | 0.500 mg |
| L-threonine | 0.125 mg |
| L-glutamic acid | 0.125 mg |
| L-phenylalanine | 0.250 mg |
| HCl 0.1 molar ad pH 3.8 to 4.0 | 0.000 mg |
| water for injection purposes | +493.025 mg | pH value of the solution reconstituted in 0.5 ml of water for injection purposes: 3.9. These injection solutions are diluted before use with 0.5 ml or 1.0 ml of a preserved, well-tolerated solution of the following composition: 5.0 mg benzyl alcohol, water for injection purposes ad 1.0 ml. Alternatively it is also possible to use solutions of benzyl alcohol (about 4–5 mg/ml) with addition of benzalkonium chloride (about 0.01–0.05 mg/ml).

Buffer capacity: 5.8 mmol/l NaOH (58 ml 0.1 N NaOH)

Titration acidity: 10 mmol/l NaOH (100 ml 0.1 N NaOH)

EXAMPLE 9

G-CSF Formulations with pH 4

| | | | |
|---|---|---|---|
| rhG-CSF | 0.175 mg | 0.175 mg | 0.175 mg |
| urea | 2.500 mg | 0.250 mg | 0.000 mg |
| sodium chloride | 1.500 mg | 1.500 mg | 1.500 mg |
| polysorbate 80 | 0.050 mg | 0.050 mg | 0.050 mg |
| aminoacetic acid analytically pure | 3.750 mg | 5.550 mg | 5.750 mg |
| L-leucine | 0.500 mg | 0.500 mg | 0.500 mg |
| L-isoleucine | 0.500 mg | 0.500 mg | 0.500 mg |
| L-threonine | 0.125 mg | 0.125 mg | 0.125 mg |
| L-glutamic acid | 0.125 mg | 0.125 mg | 0.125 mg |
| L-phenylalanine | 0.250 mg | 0.250 mg | 0.250 mg |
| water for injection purposes | +492.525 mg | +492.975 mg | +493.025 mg |
| pH value of the lyophilization form dissolved in 0.5 ml water for injection purposes | 4.0 | 4.0 | 4.0 |

Buffer capacity: 5.8 mmol/l NaOH (58 ml 0.1 N NaOH)

Titration acidity: 10 mmol/l NaOH (100 ml 0.1 N NaOH)

The formulations described in examples 1 to 9 are stable on storage not only as lyophilisates but also as injectable solutions.

What is claimed is:

1. A multidose pharmaceutical preparation comprising an aqueous solution containing a) a recombinantly produced human protein and b) 0.001–20 mg/ml of the preservative chlorobutanol, wherein said human protein has erythropoietin-like activity or granulocyte-colony stimulating factor (G-CSF)-like activity and wherein the concentration of human protein is equal to or lower than the concentration of the preservative.

2. The preparation according to claim 1, wherein the concentration of said chlorobutanol is 2–5 mg/ml.

3. A multidose pharmaceutical preparation comprising an aqueous solution containing a) a recombinantly produced human protein and b) 0.001–20 mg/ml of the preservative benzalkonium chloride, wherein said human protein has erythropoietin-like activity or granulocyte-colony stimulating factor (G-CSF)-ike activity and wherein the concentration of human protein is equal to or lower than the concentration of the preservative.

4. The preparation according to claim 3, wherein the concentration of said benzalkonium chloride is 0.01–0.05 mg/ml.

5. A multidose pharmaceutical preparation comprising an aqueous solution containing a) a recombinantly produced human protein and b) 0.001–20 mg/ml of a mixture of preservatives selected from the group consisting of chlorobutanol, benzyl alcohol, and benzalkonium chloride, wherein said human protein has erythropoietin-like activity or granulocyte-colony stimulating factor (G-CSF)-like activity and wherein the concentration of human protein is equal to or lower than the sum of the concentrations of the preservatives.

6. The preparation according to claim 5, wherein the total concentration of all the preservatives is 0.1–10 mg/ml.

7. The preparation according to claim 5, wherein the mixture contains benzalkonium chloride in combination with chlorobutanol, benzyl alcohol or chlorobutanol and benzyl alcohol.

8. The preparation according to claim 6, wherein the concentration of the preservatives is 1–5 mg/ml.

9. The preparation according to claim 7, wherein said mixture contains benzyl alcohol.

10. The preparation according to claim 9, wherein the concentration of benzyl alcohol is 4 mg/ml.

11. The preparation according to claim 10, wherein the concentration of benzalkonium chloride is lower than the concentration of benzyl alcohol.

12. The preparation according to claim 11, wherein the concentration of benzalkonium chloride is 0.02 mg/ml.

13. A multidose pharmaceutical preparation comprising an aqueous solution containing a) a recombinantly produced human protein and b) 0.001–20 mg/ml of at least one preservative selected from the group consisting of chlorobutanol, benzyl alcohol, benzalkonium chloride and mixtures thereof, wherein said human protein has granulocyte-colony stimulating factor (G-CSF)-like activity and wherein the concentration of human protein is equal to or lower than the sum of the concentrations of the preservatives.

14. The preparation according to claim 13, wherein the concentration of G-CSF is 0.01–2 mg/ml.

15. The preparation according to claim 14, wherein the concentration of G-CSF is 0.1–0.5 mg/ml.

* * * * *